United States Patent [19]

Mott

[11] Patent Number: 4,469,597

[45] Date of Patent: Sep. 4, 1984

[54] CHROMATOGRAPHIC COLUMN TERMINATOR ASSEMBLY

[76] Inventor: Lambert H. Mott, P.O. Box Drawer L, Farmington, Conn. 06032

[21] Appl. No.: 272,996

[22] Filed: Jun. 12, 1981

[51] Int. Cl.³ .............................................. B01D 15/08
[52] U.S. Cl. .................................... 210/198.2; 55/386
[58] Field of Search .................... 210/198.2, 489, 496; 55/386

[56] References Cited

U.S. PATENT DOCUMENTS

| | | | |
|---|---|---|---|
| 2,723,756 | 11/1955 | Miller et al. | 55/386 X |
| 3,201,858 | 8/1965 | Valyi | 210/496 |
| 3,310,932 | 3/1967 | Melrolber | 55/386 |
| 3,728,061 | 4/1973 | Mott | 210/489 X |
| 4,026,803 | 5/1977 | Abrahams | 210/198.2 |

*Primary Examiner*—John Adee

*Attorney, Agent, or Firm*—Prutzman, Kalb, Chilton & Alix

[57] ABSTRACT

A chromatographic column is terminated with a fitting for connecting the column to an end flow tube. The fitting is provided with a column terminator element comprising a solid rim-like housing having a central aperture therein and a duplex porous disc positioned within the aperture and secured to the housing. The porous disc comprises a main body portion providing pores having a first relatively higher micron rating and a thin layer on one surface providing pores having a relatively lower micron rating and a higher pressure drop thereacross. The thin layer is adapted to face toward the chromatographic column and the main body portion has a coarse pimpled surface opposite the planar surface to facilitate lateral fluid flow relative to the main body portion.

10 Claims, 3 Drawing Figures

CHROMATOGRAPHIC COLUMN TERMINATOR ASSEMBLY

TECHNICAL FIELD

The present invention relates generally to a chromatographic column terminator assembly and is more particularly concerned with a new and improved assembly having a unique porous terminator element therein.

BACKGROUND

As is well known, chromatography is based on the principle that different substances within a mixture can be separated from one another and concentrated into zones by passing the mixture through a two phase system. One phase of the system, such as a gas or liquid phase, acts as a carrier for the mixture while the other phase, such as solid granular absorbent powder, exerts a differential restraining force on the components of the mixture to cause separation thereof.

When using chromatographic columns to separate closely related complex substances, a sample of the material to be separated is fed through the granular absorbent packed within a long column. As the sample flows through the column the different components thereof separate and stratify so that they reach the exit end of the column in a sequential fashion. Such columns normally consist of tubes, such as stainless steel tubes, that are tightly packed with a very fine grain powdered material having a large specific surface area. Exposure of the sample to this large specific surface area causes some components of the sample to be restrained in their flow, thereby permitting the column to provide distinct and reproducible separation and resolution of the sample into its component parts as it travels through the column.

In order to obtain highly efficient separation or fractionation of the component parts of the sample, particularly where one component is present in only a small amount and is close to a major component, it is essential to provide uniform exposure of the sample across the entire cross-sectional face of the column. Maximum efficiency of a chromatographic column is obtained when the sample enters the packed column with a uniform flow profile across the entire face of the column and when the profile proceeds through the column at a uniform rate and when the carrier and sample progress in substantially a stratified or laminar fashion. If the sample is not uniformly spread across the face of the column, but instead is concentrated at the axis of the tube, it tends to exhibit a highly arcuate or crescent-shaped meniscus profile. In that event it will take longer to remove individual fractions at the exit end of the column and intermingling of the stratified layers may occur.

Additionally, at the exit end of the column, it is desirable to have the minimum possible volume between the end of the column packing and the exit tube leading to the chromatographic analyzer. Each increment of volume in the exit passage contributes to the widening of the detection band on the chromatographic read out and tends to obscure trace element peaks that may be small with respect to a major component of the sample and may occur at closely spaced locations from a major component peak in the chromatographic read out.

Conventionally, the packed chromatographic columns are sealed at each end with porous disc, usually stainless steel, placed at the very end of the column tube. One common method is to press the discs into a terminating assembly or fitting. Another technique provides a counter bore at the end of the column and the terminator disc elements are mounted directly into the counter bore at the end of the tube. In either event, the inlet and outlet tubes of the chromatographic column typically have a very small bore relative to the inside diameter of the chromatographic column and it is necessary to provide some means of distributing the sample entering the column and of collecting the sample exiting the column. As mentioned, it is extremely important to provide a uniform flow profile over the entire face of the column both at the entrance end of the column from the very small bore of the inlet flow tube and also at the outlet or exit end of the column. Heretofore this distribution was accomplished through the the use of a small screen that permitted lateral flow between the wires of the screen. These screens were required in addition to the porous discs that were used to retain the packing within the chromatographic columns.

DISCLOSURE OF THE INVENTION

It has now been found that the use of both a porous and distributing screen can be obviated through the use of a single duplex structure, thereby eliminating an extra component in the assembly and the additional cost associated therewith. Additionally, it has been found that this can be achieved while effecting a minimum void volume and a uniform flow profile across the entire face of the chromatographic column, thereby assuring an extremely efficient distribution of the sample and fractionation thereof by the chromatographic column. The device of the present invention can be advantageously used at both ends of the chromatographic column and substantially reduces the free volume within the terminator assembly, in fact resulting in a free volume that is only that of the porosity of the duplex porous structure itself.

Other features of the invention will be in part obvious and in part pointed out more in detail hereinafter.

These and related advantages are achieved in accordance with the present invention by providing a column terminator element comprised of a duplex porous frit member mounted within the central aperture of a solid rim-like housing. The duplex frit is secured to the housing and comprises a main body portion having a first relatively higher micron rating and a coarse pimpled surface on one planar surface thereof. A thin layer having a relatively lower micron rating is secured to the planar surface of the main body portion opposite the coarse pimpled surface. The thin layer faces toward the interior of the chromatographic column at either end thereof and is spaced from the pimpled surface by substantially the entire thickness of the main body portion. The pimpled surface effectively facilitates lateral fluid flow of the sample relative to the main body portion to provide the requisite uniform profile across the entire face of the chromatographic column.

A better understanding of the advantages, features, properties and relationships of the invention will be obtained from the following detailed description and accompanying drawings which set forth an illustrative embodiment and are indicative of the way in which the principles of the invention are employed.

BEST MODE FOR CARRYING OUT THE INVENTION

Figure 1:
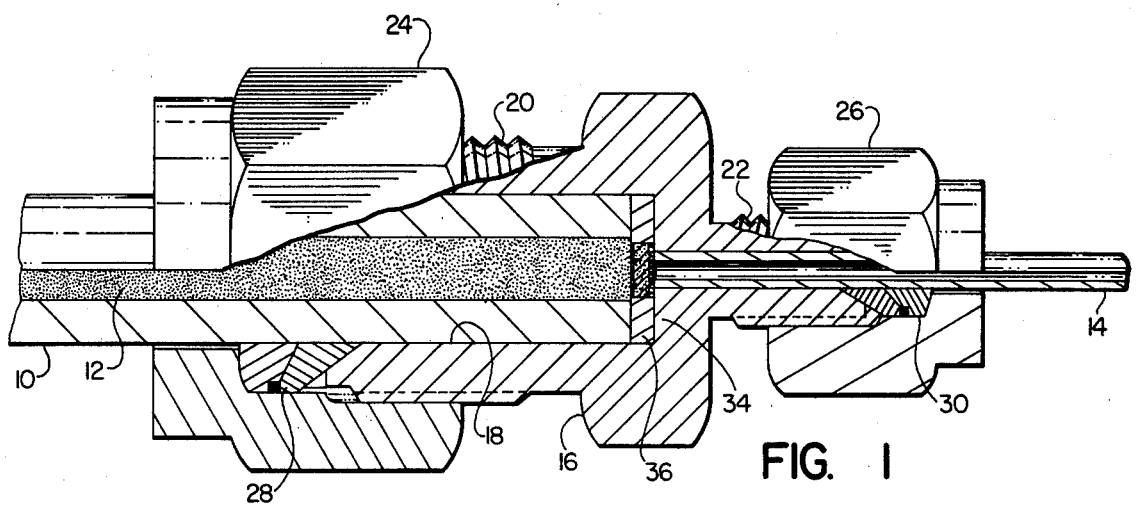
FIG. 1 is a side elevational view, partially broken away and partially is section of one end of a chromatographic column having a column terminator assembly of the present invention mounted thereon.

Referring now to the drawings in greater detail wherein like reference numerals indicate like parts throughout the several figures, one end of a chromatographic column is shown in FIG. 1 with a terminator assembly mounted thereon. The column takes the form of a tubing 10, such as a stainless steel tubing, with its interior filled with a granular particulate absorbent material 12. A fluid flow tube 14 of substantially reduced diameter is connected to the end of the column by a suitable end fitting which, in the embodiment illustrated, is of the compression seal reducing type. This fitting includes a reducing union 16 adapted to receive the butt ends of both the column 10 and the tubing 14 within the coaxially extending stepped bore 18 thereof. The exterior of the union is provided with threads 20, 22 on opposite ends thereof for engagement by the locking nuts 24, 26 respectively that bear against and compress shim-like gaskets, generally designated 28, 30, abutting the opposite free ends of the union 16.

As illustrated, the bore 18 of the reducing union 16 is provided with an abrupt shoulder 34 between the small bore portion sized to receive the flow tube 14 and the opposite enlarged bore portion sized to receive the substantially larger tubing 10 of the chromatographic column. Mounted within the large bore portion at the shoulder 34 and abutting thereagainst is a chromatographic column terminator element 36 constructed in accordance with the present invention. The element 36 includes a solid metal, washer-like rim or housing member 38 having an outside diameter substantially equal to the outside diameter of the tube 10 forming the chromatographic column. The rim or housing 38 is provided with a central aperture having a diameter substantially equal to but preferably slightly smaller than the outside diameter of the chromatographic column tubing 10. Thus the radial dimension of the solid portion of the housing 38 is substantially equal to but slightly greater than the wall thickness of the tube 10. Since the outside diameter of the fluid flow-tube 14 is typically less than the inside diameter of the chromatographic column, the diameter of the central aperture within the rim-like housing is preferably of a size that falls between these two dimensions and preferably is of a size substantially equal to the inside diameter of the chromatographic column so that no portion of the sample is restricted in its flow at either end of the chromatographic column. The rim-like housing 38 rests firmly against the shoulder 34 of the reducing union and, in turn, the butt end of the chromatographic tubing 10 engages the solid rim or housing and sandwiches the terminator element 36 therebetween.

Figure 2:
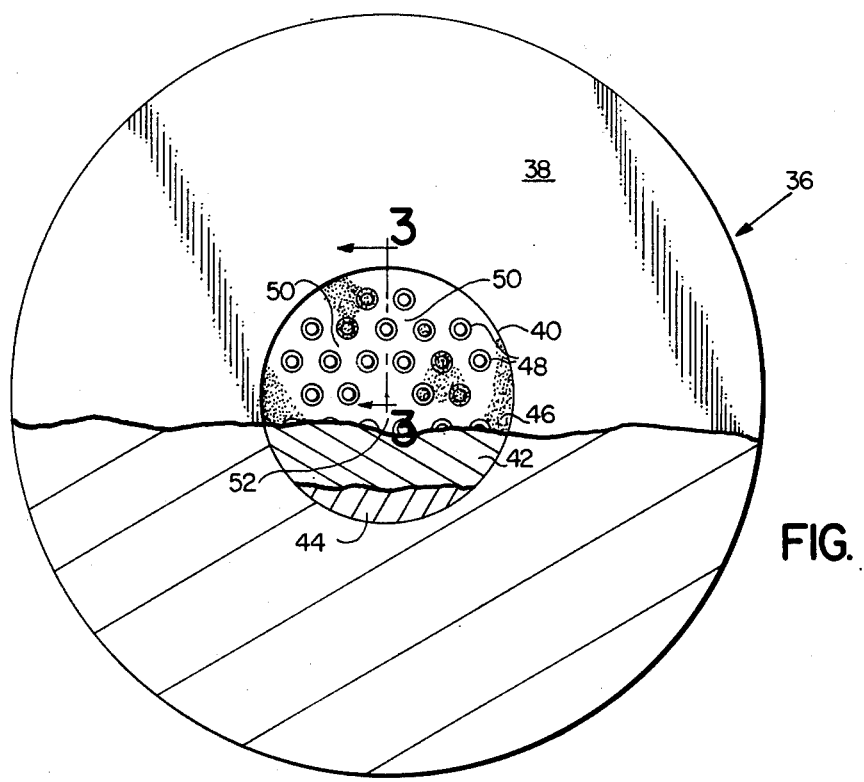
FIG. 2 is an enlarged end view of a portion of a column terminator element used in the assembly of FIG. 1
Figure 3:
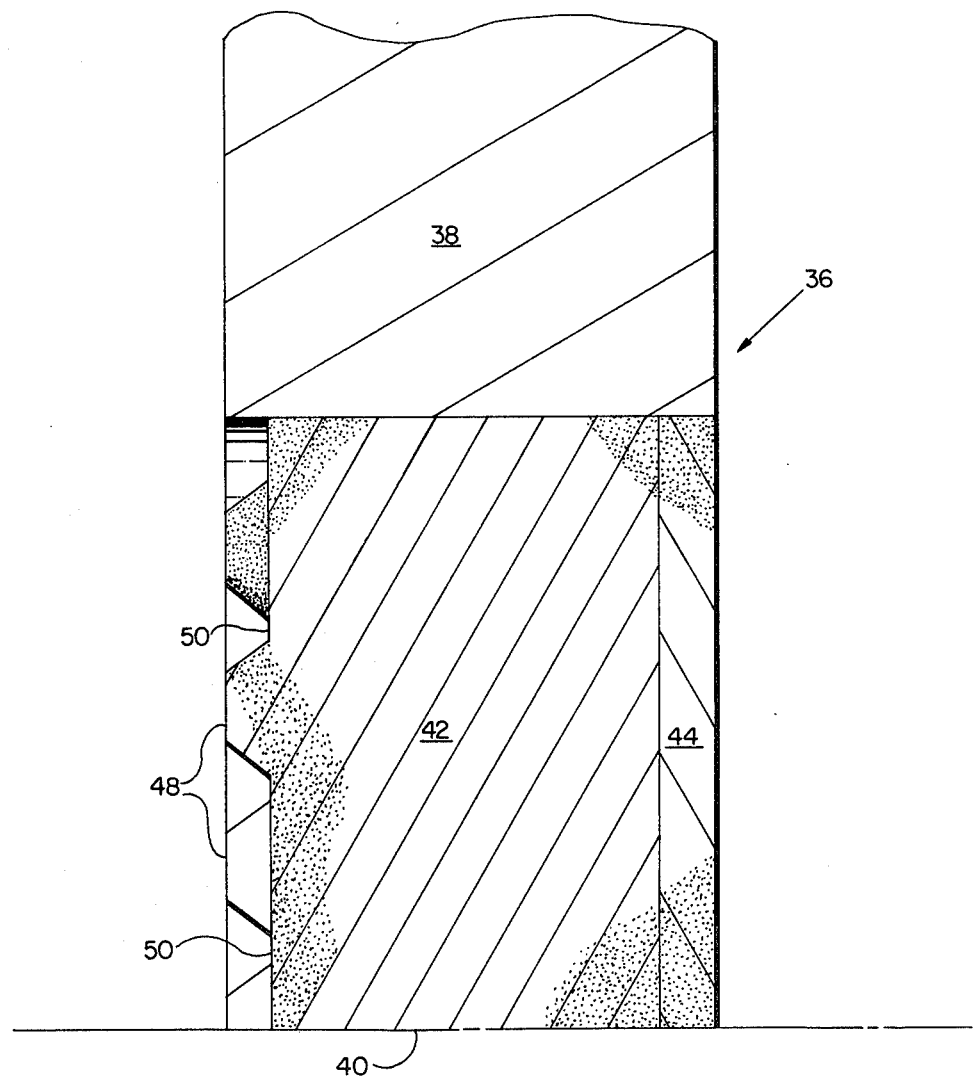
FIG. 3 is a further enlarged sectional view taken along the line 3—3 of FIG. 2 and illustrating the structure of the duplex porous terminator element of the present invention.

Positioned within the central aperture of the rim-like housing 38 and bonded thereto is a porous sintered metal frit or disc 40 which, as best seen in FIG. 3, is of duplex construction. The frit 40 comprises a porous main body portion 42 having a thickness only slightly less than the thickness of the rim-like housing member 38 and a very thin layer 44 integrally coextensive with one planar end face thereof. The main body portion 42 is provided with a coarse pimpled surface 46 on its planar end face opposite the layer 44. The pimples 48 forming the surface 46 are disturbed over the end surface in the form of a patterned grid and are composed of the same material as the main body portion 42 from which they project uniformly. In the specific embodiment shown in FIGS. 2 and 3, the pimples 48 are formed as tapered frusto-conical spaced projections. The pimples are of uniform size and configuration and exhibit a diameter at their crowns that is approximately one half the diameter of their base. As will be appreciated, other configurations and sizes may be employed.

The pimples 48 project only a few thousandths of an inch beyond the main body portions and define therebetween a plurality of intersecting channels 50 of uniform depth that readily permit lateral fluid flow relative to the main body portion. As best seen in FIG. 2, the central portion 52 of the coarse face 46 is free of any pimples, while the pimples located on the outer perimeter of the disc are spaced about the perimeter so that the butt end of the effluent flow tube 14 will rest on their flat crown surfaces, permitting flow of the sample material around the pimples so as to uniformly distribute itself across the face of the main body portion at the entrance end of the chromatographic column and to flow smoothly from the main body portion and effect minimum obstruction at the exit flow tube of the chromatographic column assembly.

In contrast to the coarse pimpled surface 46, the very thin layer 44 integrally formed on the opposite planar face of the main body member provides a relatively smooth exterior surface. This smooth layer faces inwardly toward the absorbent particles within the chromatographic column to effectively close the column against the loss of that material. The thin layer 44 has a thickness approximately equal in size to the height of the pimples 48 projecting from the opposite face of the main body member. The thin character of the layer is preferred since the layer preferably has a relatively lower micron rating and a relatively higher pressure drop thereacross than the material of the main body member. The thinness of the layer 44 maintains the amount of high pressure drop material at a minimum while still maintaining the differential in micron rating between the layer 44 and the main body portion 42.

Both the main body portion 42 and the thin layer 44 on one face thereof are preferably porous, sintered metal members, fabricated in accordance with known procedures to provide the desired substantially different physical characteristics within each component or portion of the duplex element or disc. An example of such a multi-layer structure can be found in my earlier U.S. Pat. No. 3,728,061 issued Apr. 17, 1973 and entitled "Multi-Layer Spineret with Head Filter". The metal or alloy used for each portion of the duplex element may be the same or may be different, depending on the specific use of the element. For example, the duplex element may be made from bronze, copper, nickel, monel, inconel, hastelloy or precious metals such as silver, gold or platinum. However, for most applications, it is generally preferred that the sintered duplex disc be fabricated from stainless steel and that both portions of the duplex element be fabricated from the same material.

As is known, the micron rating of a material indicates the impermeability of that material to particles having a size corresponding to or greater than the rating number. Although the micron rating relates to the pore size of the pores within these sintered members, the micron rating and pore size are not synonymous. It is possible for members having a pore size larger than dispersed particles within a fluid dispersion to filter those particles from the dispersion and retain those particles within the porous member. Thus, it is preferred that the material be described with respect to its micron rating rather than its pore size.

It is also known that the particle size of the stainless steel powder used to fabricate the porous element exhibits a relationship to the micron rating. However, this relationship will vary depending on the compression to which the stainless steel powder is subjected during the sintering operation. Of course the material exhibiting the smaller micron rating will typically also exhibit a higher pressure drop than the material exhibiting a higher micron rating. Accordingly, in the duplex element of the present invention, it is preferred that the micron rating of the main body portion be measurably and significantly greater than the micron rating of the thin layer. For example, using a frit having a total thickness of thirty two thousandths of an inch with a thin layer thickness of five to ten thousandths, the main body portion may exhibit a micron rating of 10 to 20 microns while the thin layer could have a rating of 0.5 to 2 microns. As can be appreciated, the specific micron rating can be varied as desired. The lower micron rating material typically exhibits a higher pressure drop across the thickness of the material and for this reason it is desired that the layer 44 be as thin as possible while still providing the desired differential in micron rating.

It is also preferred, in accordance with the present invention, that the duplex element exhibit a minimum void volume so that a minimum amount of sample is held within the element at any particular time and closely associated peaks in the chromatographic spectrum can be isolated and identified more effectively. Since the pressure drop across the thin layer is considerably higher than across the main body portion, the thin layer will provide a greater deterrent to flow. However, as mentioned, the thinness of this layer prevents this from being a disadvantage. Instead, the effluent flow from the chromatographic column will flow in a uniform profile across the thin layer 44 and, upon reaching the main body 42, will immediately pass though the main body at a substantially faster rate, thus assuring both axial and lateral flow toward the substantially narrower diameter tubing. The sample flows both through and around the pimples 48 and along the channels 50 so that substantially all of each separated component will very rapidly flow towards the exit flow tube. Similarly, at the entrance end of the chromatographic column, the flow of the sample onto the main body portion permits the sample to distribute itself rapidly across the coarse pimpled face of the main body portion and flow rapidly therethrough until it reaches the thin layer 44. At this layer it further and fully distributes itself as it flows toward and into the chromatographic column, thus assuring a uniform profile of the sample across the entire face of the chromatographic column before it flows through the body of the column. This operation is achieved despite the fact that the substantially smaller inlet and exit flow tubes rest directly against the pimples 48 of the main body portion. As can be appreciated, the pimples provide an offset which permits rapid lateral fluid flow around the pimples and through the channels so as to fully distribute the sample either across the full face of the thin layer at the entrance end of the column or permit rapid collection of the separated segments of the sample at the exit tube of the column. Thus the duplex disc provides efficient smooth operation while eliminating the need for the separate distributor screen employed heretofore.

I claim:

1. A chromatographic column terminator element for use in a fitting connecting a chromatographic column with an end flow tube comprising a solid rim-like housing member having a central aperture therein and a duplex porous frit member positioned within said aperture and secured to said housing, said duplex frit member comprising a main body portion providing pores having a first relatively higher micron rating and a thin layer on one surface of the main body portion providing pores having a relatively lower micron rating, said thin layer being adapted to face toward said chromatographic column, said main body portion having a coarse pimpled surface on the face of said body portion opposite said thin layer, said pimpled surface being adapted to facilitate lateral fluid flow relative to said main body portion.

2. The chromatographic column terminator element of claim 1 wherein said duplex frit member is a sintered porous metal disc with said main body portion being substantially thicker than said layer, said coarse pimpled surface being comprised of an array of projections extending from the main body portion, said projections being spaced to provide a plurality of interconnected channels therebetween facilitating said lateral fluid flow.

3. The chromatographic column terminator element of claim 1 wherein said main body portion provides a relatively lower pressure drop therethrough than said thin layer, said coarse pimpled surface being comprised of a grid of integral pimples projecting from the surface of said main body portion.

4. The chromatographic column terminator of claim 3 wherein said pimples have tapered side walls defining interconnected fluid flow channels therebetween.

5. The chromatographic column terminator element of claims 1, 2 or 3 wherein the pimples forming the coarse pimpled surface provide pores having the same micron rating as the pores of said main body portion.

6. The chromatographic column terminator element of claim 1 wherein said coarse pimpled surface is comprised of a grid of truncated projections extending from the main body portion, said grid being pimple-free at its center.

7. The column terminator element of claim 1 mounted within a compression seal fitting for terminating one end of a chromatographic column, said fitting having an internal shoulder, said element being in firm abutting engagement with said shoulder.

8. The chromatographic column terminator element of claim 1 wherein said frit is positioned within said aperture and bonded to said rim-like housing.

9. The chromatographic column terminator element of claim 1 wherein said coarse pimpled surface is adapted to abuttably engage one end of an end flow tube of reduced diameter.

10. The chromatographic column terminator element of claim 1 wherein said duplex frit member is a sintered porous metal disc of controlled porosity and permeability.

* * * * *